US011382535B2

(12) United States Patent
Senegas et al.

(10) Patent No.: US 11,382,535 B2
(45) Date of Patent: Jul. 12, 2022

(54) DETECTION AND MEASUREMENT OF BREATHING USING AN OPTICAL CAMERA AND PROJECTED SHADOWS

(71) Applicant: KONINKLIJKE PHILIPS N.V., Eindhoven (NL)

(72) Inventors: Julien Senegas, Hamburg (DE); Sascha Krueger, Hamburg (DE); Daniel Wirtz, Hamburg (DE); Vincent Jeanne, Migne Auxances (FR); Thirukamaran Thangaraj Kanagasabapathi, Eindhoven (NL); Gerrit Maria Kersten, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 528 days.

(21) Appl. No.: 16/340,707

(22) PCT Filed: Oct. 11, 2017

(86) PCT No.: PCT/EP2017/075997
§ 371 (c)(1),
(2) Date: Apr. 10, 2019

(87) PCT Pub. No.: WO2018/069419
PCT Pub. Date: Apr. 19, 2018

(65) Prior Publication Data
US 2019/0307367 A1      Oct. 10, 2019

Related U.S. Application Data

(60) Provisional application No. 62/406,458, filed on Oct. 11, 2016.

(51) Int. Cl.
*A61B 5/113*      (2006.01)
*A61B 5/00*       (2006.01)
(Continued)

(52) U.S. Cl.
CPC ............ *A61B 5/113* (2013.01); *A61B 5/0033* (2013.01); *A61B 5/0077* (2013.01);
(Continued)

(58) Field of Classification Search
None
See application file for complete search history.

(56) References Cited

U.S. PATENT DOCUMENTS 5,107,845 A    4/1992  Guern et al.
7,431,700 B2  10/2008  Aoki et al.
(Continued)

FOREIGN PATENT DOCUMENTS

JP    2012085915 A2 *  1/2012
JP    2012085915 A     5/2012
(Continued)

OTHER PUBLICATIONS

Written Opinion and International Search Report dated Jan. 3, 2018.

*Primary Examiner* — Amelie R Davis
*Assistant Examiner* — Marjan Saboktakin

(57) ABSTRACT

A respiratory monitoring device comprises: a light source (30) arranged to generate a projected shadow (S) of an imaging subject (P) positioned for imaging by an imaging device (8); a video camera (40) arranged to acquire video of the projected shadow; and an electronic processor (42) programmed to extract a position of an edge of the projected shadow as a function of time from the acquired video. In some embodiments, the light source is arranged to project the shadow onto a bore wall (20) of the imaging device, and the video camera is arranged to acquire video of the projected shadow on the bore wall. The electronic processor may be programmed to extract the position of the edge (E) as a one-dimensional function of time (46) based on the (Continued)

position of the edge in each frame of the acquired video and time stamps of the video frames.

13 Claims, 4 Drawing Sheets

(51) Int. Cl.
| | |
|---|---|
| A61B 5/08 | (2006.01) |
| A61B 6/00 | (2006.01) |
| A61B 5/11 | (2006.01) |
| A61B 5/055 | (2006.01) |
| A61B 6/03 | (2006.01) |
| G01R 33/567 | (2006.01) |
| G01R 33/565 | (2006.01) |
| G01R 33/28 | (2006.01) |

(52) U.S. Cl.
CPC .......... *A61B 5/0816* (2013.01); *A61B 5/1128* (2013.01); *A61B 6/032* (2013.01); *A61B 6/527* (2013.01); *A61B 6/541* (2013.01); *G01R 33/283* (2013.01); *G01R 33/5673* (2013.01); *G01R 33/56509* (2013.01); *A61B 5/055* (2013.01); *A61B 5/7292* (2013.01); *A61B 6/037* (2013.01)

(56) References Cited

U.S. PATENT DOCUMENTS

| | | | |
|---|---|---|---|
| 9,655,554 B2 | 5/2017 | Bindszus et al. | |
| 10,178,957 B2 | 1/2019 | Schmeitz et al. | |
| 2003/0188757 A1 | 10/2003 | Yanof et al. | |
| 2004/0082874 A1* | 4/2004 | Aoki | A61B 5/4818 600/534 |
| 2006/0025672 A1 | 2/2006 | Sendai | |
| 2009/0187112 A1* | 7/2009 | Meir | G06T 7/593 600/534 |
| 2013/0324875 A1 | 12/2013 | Mestha et al. | |
| 2014/0334697 A1* | 11/2014 | Kersten | A61B 5/02416 382/128 |

FOREIGN PATENT DOCUMENTS

| | | | | |
|---|---|---|---|---|
| WO | 2009075559 A2 | 6/2009 | | |
| WO | WO-2009075559 A2 * | 6/2009 | | G16H 40/67 |

* cited by examiner

DETECTION AND MEASUREMENT OF BREATHING USING AN OPTICAL CAMERA AND PROJECTED SHADOWS

CROSS REFERENCE TO RELATED APPLICATIONS

This application is a U.S. national phase application of International Application No. PCT/EP2017/075997 filed on Oct. 11, 2017, which claims the benefit of U.S. Provisional Application Ser. No. 62/406,458 filed on Oct. 11, 2016 and is incorporated herein by reference.

FIELD

The following relates generally to the medical imaging arts, respiratory monitoring arts, respiratory-gated medical imaging arts, and related arts.

BACKGROUND

Monitoring of patient respiration during medical imaging can serve various useful purposes. Monitored respiratory cycling can be used to perform prospective gated imaging, in which imaging data are only collected during a certain portion (i.e. phase) of the respiratory cycle, which can reduce motion artifacts due to the respiration. In an alternative retrospective gating approach, imaging data are collected continuously and then binned by respiratory phase, and a chosen phase may be reconstructed. Respiratory monitoring can also be used to detect breath-holds, e.g. for triggering imaging while the patient holds his or her breath. Respiratory monitoring can also serve a patient safety monitoring function, e.g. if respiration becomes erratic the imaging session can be interrupted or terminated.

Various respiratory monitoring devices are known. In some approaches, a resistive belt is used to detect changes in chest or torso diameter with inhalation/exhalation. An accelerometer can be similarly used to monitor chest motion, or an air flow meter can be used to directly monitor air flow into/out of the mouth or nasal passages. However, these approaches require connecting a monitoring device with the patient this may be uncomfortable for the patient, especially if other devices are also connected. The device also takes up examination region space. Furthermore, the respiratory monitoring device might not be compatible with certain imaging modalities. For example, metallic components are sometimes incompatible with magnetic resonance (MR) imaging while x-ray absorbing materials are problematic in computed tomography (CT) imaging.

Another known respiratory monitor device employs a video camera arranged to acquire video of the patient during the imaging. Respiration is extracted from the image frames by analysis of the image to detect the chest motion. Dedicated lighting may optionally be provided to improve lighting for the video. Difficulties with this approach include arrangement of the camera to view the patient without obstruction, usually from above, and complex image processing performed to extract the chest motion. The approach is also susceptible to error due to small patient/camera misplacement, and/or due to low image contrast, e.g. if the patient is wearing an all-white hospital gown, and may be unusable if the patient is lying in supine position such that the chest is not observable, and/or if the chest is covered by an obscuring component such as a local radio frequency (RF) coil (as in some MR imaging procedures).

The following discloses a new and improved systems and methods that address the above referenced issues, and others.

SUMMARY

In one disclosed aspect, a respiratory monitoring device comprises: a light source arranged to generate a projected shadow of an imaging subject positioned for imaging by an imaging device; a video camera arranged to acquire video of the projected shadow; and an electronic processor programmed to extract a position of an edge of the projected shadow as a function of time from the acquired video. In some embodiments, the light source is arranged to project the shadow onto a bore wall of the imaging device, and the video camera is arranged to acquire video of the projected shadow on the bore wall. The electronic processor may be programmed to extract the position of the edge as a one-dimensional function of time based on the position of the edge in each frame of the acquired video and time stamps of the video frames.

In another disclosed aspect, a respiratory monitoring device comprises: an imaging device having a bore wall; a light source arranged to project a shadow of an imaging subject positioned for imaging by the imaging device onto the bore wall of the imaging device; a video camera arranged to acquire video of the shadow of the imaging subject projected on the bore wall; and an electronic processor programmed to extract a position of an edge (E) of the shadow projected onto the bore wall as a function of time from the acquired video.

In another disclosed aspect, a respiratory monitoring method comprises: projecting a shadow of an imaging subject positioned for imaging by an imaging device; acquiring video of the projected shadow; extracting a position of an edge of the projected shadow as a function of time from the acquired video; and extracting respiratory information from the extracted position of the edge of the projected shadow as a function of time.

One advantage resides in providing camera-based respiratory monitoring during medical imaging with improved accuracy due to improved image contrast.

Another advantage resides in providing such improved image contrast even when the patient is wearing low-contrast clothing.

Another advantage resides in providing camera-based respiratory monitoring that is compatible with a patient lying in supine (i.e. face-down) position.

Another advantage resides in providing camera-based respiratory monitoring with reduced data processing complexity.

Another advantage resides in providing camera-based respiratory monitoring with reduced monitoring hardware located in the examination region.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

FIG. 1 diagrammatically shows a medical imaging device including a camera-based respiratory monitoring device as disclosed herein.

DETAILED DESCRIPTION

Figure 1:
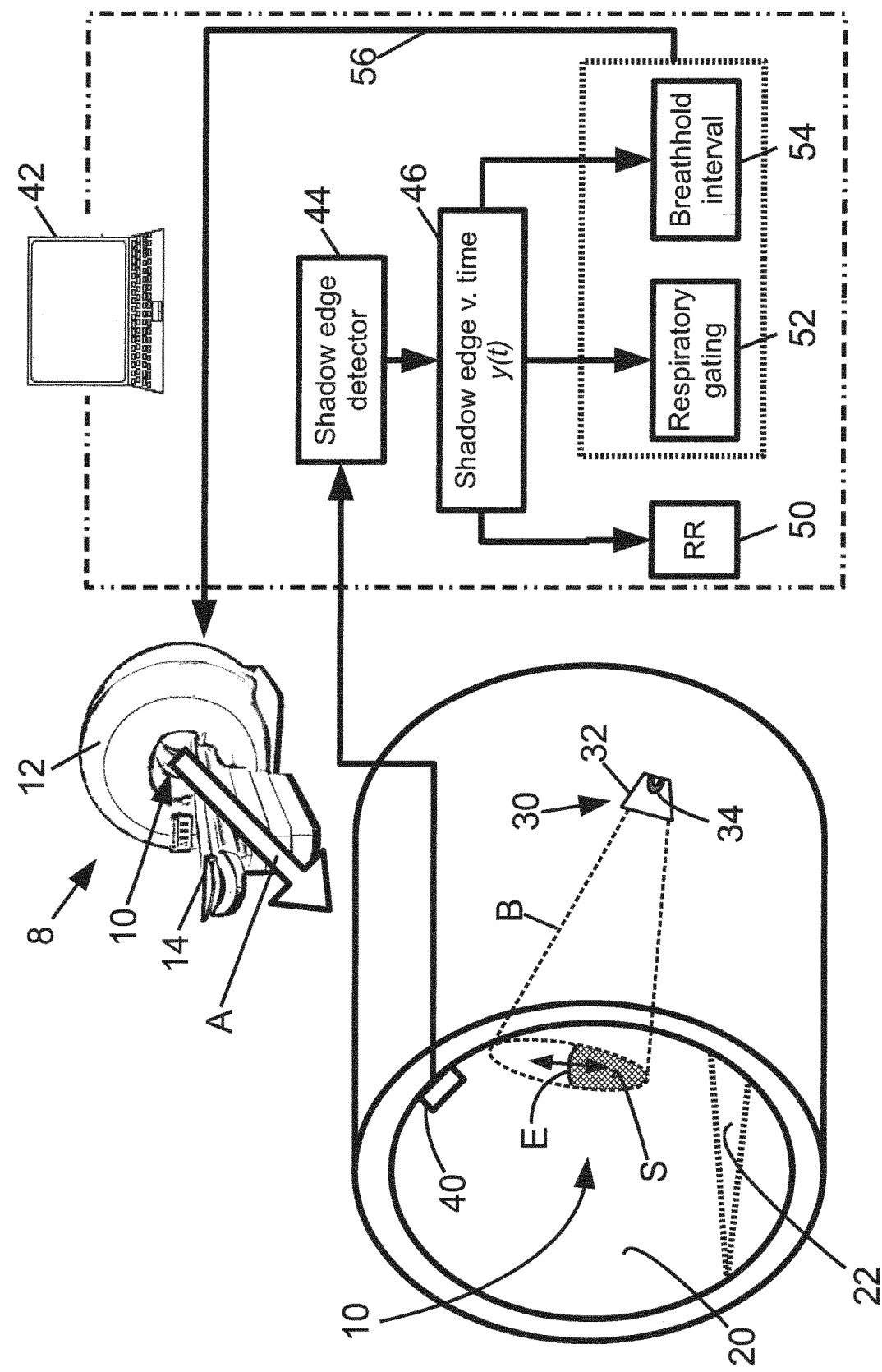

Camera-based respiratory monitoring devices disclosed herein are based on the insight made herein that many difficulties with existing camera-based respiratory monitoring devices can be overcome by acquiring video of a shadow of the chest projected onto a nearby surface, rather than imaging the patient's chest directly. Conveniently, in many medical imaging devices the examination region is defined by a scanner bore, and the bore wall thus serves as a convenient surface onto which the shadow of the chest may be projected. For example, many magnetic resonance (MR) imaging devices employ a horizontal solenoidal magnet and the examination region is located inside the bore of this solenoidal magnet. Likewise, many computed tomography (CT) imaging devices employ an x-ray source and opposing x-ray detector assembly that revolve in concert around the patient, and a bore surrounds the examination region containing the patient to ensure safe isolation of the patient from the rapidly revolving x-ray components. Yet again, in many positron emission tomography (PET) imaging devices the PET detectors form one or more annular rings surrounding the examination region, and again a bore is provided to isolate the patient from the sensitive PET detectors. In each such design, the bore is designed to have a smooth generally cylindrical wall to avoid the potential for injury to the patient, and this smooth bore wall makes a suitable "projection screen" onto which the shadow of the chest is projected.

Advantages of acquiring video of the projection of the patient's chest onto the bore wall (or other "projector screen") are many. With suitable lighting, the edge of the chest shadow provides a well-defined and high contrast edge that is easily detected in the video frames using known edge detection algorithms. The edge of the chest shadow is also geometrically simple, and for a patient lying in a prone or supine position can be expected to move up with inhalation as the chest expands and down with exhalation as the chest contracts. Thus, the detected motion is a simple one-dimensional up/down motion of an edge in a well-defined planar (or approximately planar) projection plane. By contrast, conventional camera-based respiratory monitoring that images the chest directly generally requires detecting a high contrast feature on the chest (which may be unavailable, e.g. if the patient is wearing an all-white hospital gown) and performing image processing to estimate the motion of that feature in three-dimensional space based on the acquired two-dimensional image frames.

Another advantage of imaging the edge of the projected chest shadow is that the respiration can be monitored with the patient in either prone (i.e. face-up) or supine (i.e. face-down) position. In the latter case of supine position, the projected shadow is not of the chest but rather of the back or shoulders. Even in supine position, the back and shoulders of the patient tend to rise and fall with inhalation/exhalation, providing a detectable cycling of the shadow edge. Similarly, the disclosed approach remains usable if the patient has a local radio frequency (RF) coil (or coil array) disposed on the chest (or back) for MR imaging, so long as the local RF coil (array) is resting on the chest (or back, or shoulder) and is free to move up and down with inhalation/exhalation. As yet another advantage, it may be easier to position the camera to image the projected shadow edge as compared with the chest itself, especially in a confined small-diameter imaging device bore.

With reference to FIG. 1, an illustrative magnetic resonance (MR) imaging device 8 is of the horizontal solenoidal magnet type, and defines a horizontal cylindrical bore 10 surrounded by the magnet housing 12, which may for example comprise a magnet cryostat containing the (e.g. superconducting) magnet. A patient or other imaging subject is loaded onto a couch or other subject support 14 which has a sliding tabletop for moving the imaging subject into the bore 10.

As indicated by arrow A, an enlarged view of the bore 10 is shown in FIG. 1. The bore 10 is a cylindrical bore having an inside cylindrical wall 20. While the bore 10 is expected to be generally cylindrical, it may have substantial deviations from an ideal cylinder; for example, a contemplated flat bottom portion 22 is shown in dotted lines, which flat bottom 22 may optionally be provided, for example, as a supporting surface for the sliding tabletop of the subject support 14. The bore wall 20 may deviate from an ideal cylinder in other ways, such as including flared ends, or having a longitudinal slot (e.g. in a so-called "open" MR device). It should also be noted that "cylindrical" does not require a circular cross-section, for example the cylindrical bore 10 may have a non-circular oval cross-section. Typically, although not necessarily, the bore wall 20 is designed to be smooth so as to reduce likelihood of injury of the imaging subject moved into the bore 10.

While the illustrative imaging device is an MR imaging device 8, as previously noted other types of imaging devices also have cylindrical bores as just described. For example, a computed tomography (CT) imaging device or a positron emission tomography (PET) imaging device has a similar cylindrical bore 10 with an inner cylindrical bore wall 20, albeit for different design reasons, e.g., the CT bore wall isolates the imaging subject from the rapidly rotating x-ray/x-ray detector assemblies, while the PET bore wall isolates the imaging subject from sensitive and possibly high voltage PET detectors. Regardless of these modality-specific particularities, the bore 10 is designed to have a smooth, cylindrical wall 20 (or at least a large portion of the bore wall 20 is smooth and cylindrical, e.g. excepting the optional flat bottom 22) to avoid the potential for injury to the patient. As disclosed herein, and this smooth bore wall 20 makes a suitable "projection screen" onto which a shadow of the imaging subject is suitably projected.

To this end, a light source 30 is arranged to generate a projected shadow S of an imaging subject positioned for imaging by the imaging device 8. (Note that in the perspective view of FIG. 1 the light source 30 would be occluded from view by the bore 10 if the magnet housing 12 is opaque, but is shown diagrammatically for illustrative convenience). An edge E of the shadow S can be expected to move generally up and down with respiration. Specifically, during inhalation the chest expands causing the shadow edge E to move generally upward, and during exhalation the chest (partially) deflates causing the shadow edge E to move generally downward. (Note that while this is easiest to visualize for a patient lying in a prone position with the shadow S being of the chest, such expansion/deflation and consequent upward/downward movement is also expected for a patient lying in a supine position for which the shadow S is of the back or shoulders). To improve contrast of the shadow S and sharpness of the edge E, the illustrative light source 30 is optionally a directional light source having a projection optic 32 shaping light from a light emission source 34 into a beam B. The projection optic 32 may be, by way of illustration, a conical, parabolic or other beam-forming directional reflector, a convex lens or other beam-forming directional lens, a combination of such a directional reflector and lens, or so forth. The light emission source 34 may, for example, be a light emitting diode (LED) or array of LEDs, an incandescent lamp, a halogen lamp, or so forth.

A video camera 40 is arranged to acquire video of at least a portion of the projected shadow S including edge E. The video camera 40 can be any imaging device capable of acquiring a sequence of images (that is, a sequence of video frames), and preferably is a digital video camera that outputs digital video frames with a time stamp annotating each frame. An electronic processor 42 is operatively connected to receive the video stream (that is, the sequence of video frames). For example, the illustrative electronic processor 42 is a computer 42 that may be operatively connected with the video camera 40 by a USB cable or other high speed data transmission cable. The electronic processor 42 is programmed to extract a position of the edge E of the projected shadow S as a function of time from the video acquired by the video camera 40. This processing is diagrammatically indicated in FIG. 1 as a shadow edge detector 44, which can operate on a per-frame basis using any suitable edge-detection algorithm, e.g. by computing a gradient image and detecting a high gradient line corresponding to the shadow edge E; or detecting a transition line separating lower intensity shadow S and the higher intensity region illuminated by the unoccluded beam B; or so forth. Since the shadow edge E is generally a line (possibly curved), the position of the shadow edge in a given frame acquired at time t (as indicated by the frame time stamp t) can be represented as a scalar value y(t) representing the shadow edge versus time 46, so that when this processing is repeated for a time sequence of video frames the output is a function y(t) over the time interval of the video (which may be acquired continuously at a frame rate of, e.g. 24 frames per second (fps; standard for movie recording) or 30 fps (standard video frame rate). Since the typical respiration rate is on the order of 12-20 breaths per minute (i.e. one breath every 3-5 sec), any frame rate of at least a few frames per second is fast enough to provide respiratory cycling information in the form of the shadow edge versus time function 46 with suitable precision. From this function 46, the respiration rate 50 can be readily derived as the peak-to-peak time interval of y(t). By analyzing the waveform shape of the function y(t) the overall respiratory cycle can be obtained (with end-inhalation points corresponding to the peaks of y(t) and end-exhalation points corresponding to the valleys of y(t), and this provides a respiratory gating signal 52 (that is, a representation of the respiration phase as a function of time). Additionally or alternatively, a breath-hold interval 54 can be detected as a time interval during which y(t) is constant (and typically close to its peak value corresponding to end-inhalation since usually the patient inhales and then holds breath). As indicated by data flow arrow 56, these data 52, 54 may optionally be used as inputs to the imaging device 8 to perform gated imaging (using respiratory gating signal 52) or to time data acquisition with the detected breath-hold interval 54.

Figure 2:
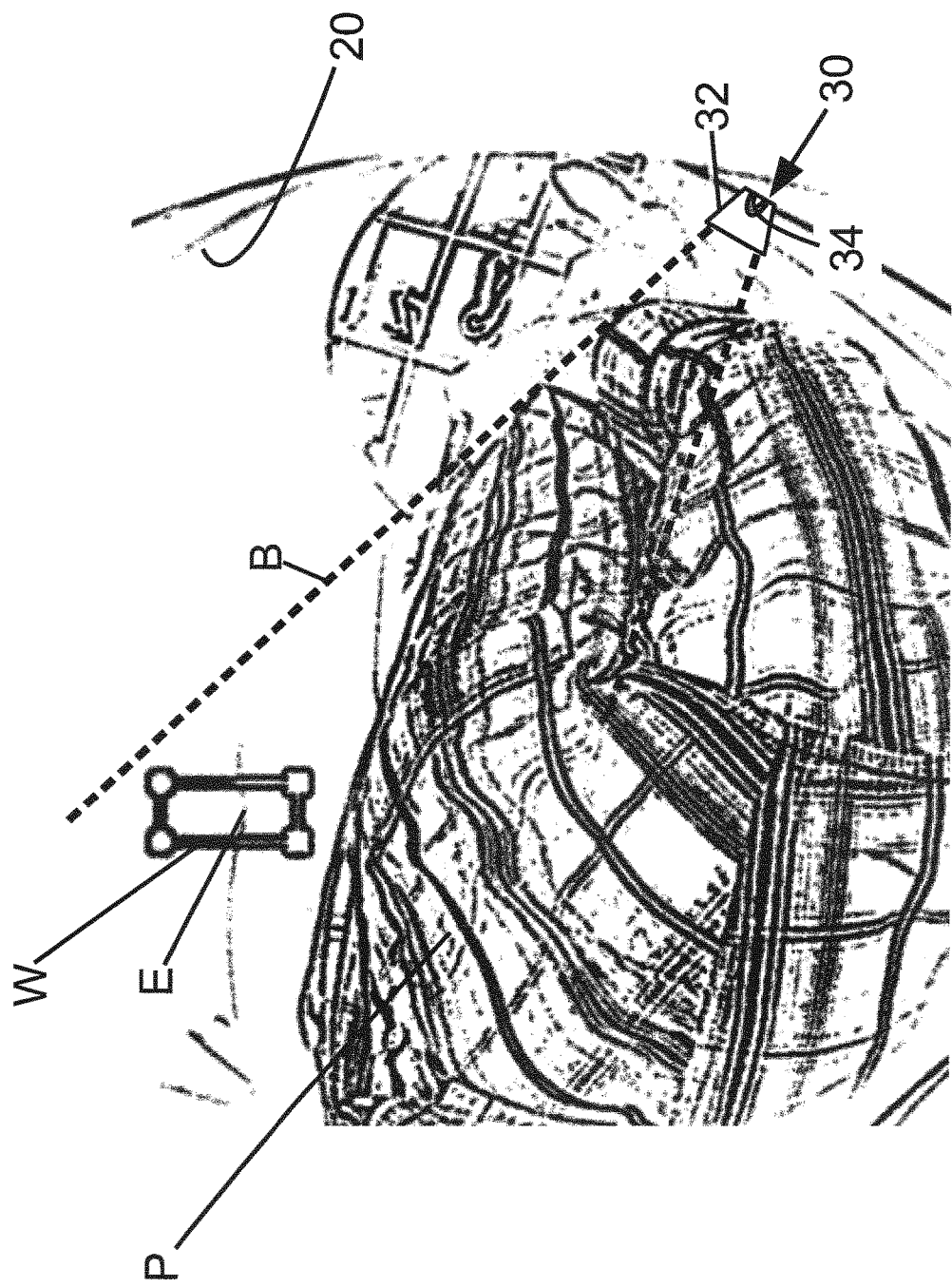
FIG. 2 diagrammatically shows a perspective view of a suitable placement of the light source of the respiratory monitoring device of FIG. 1.
Figure 3:
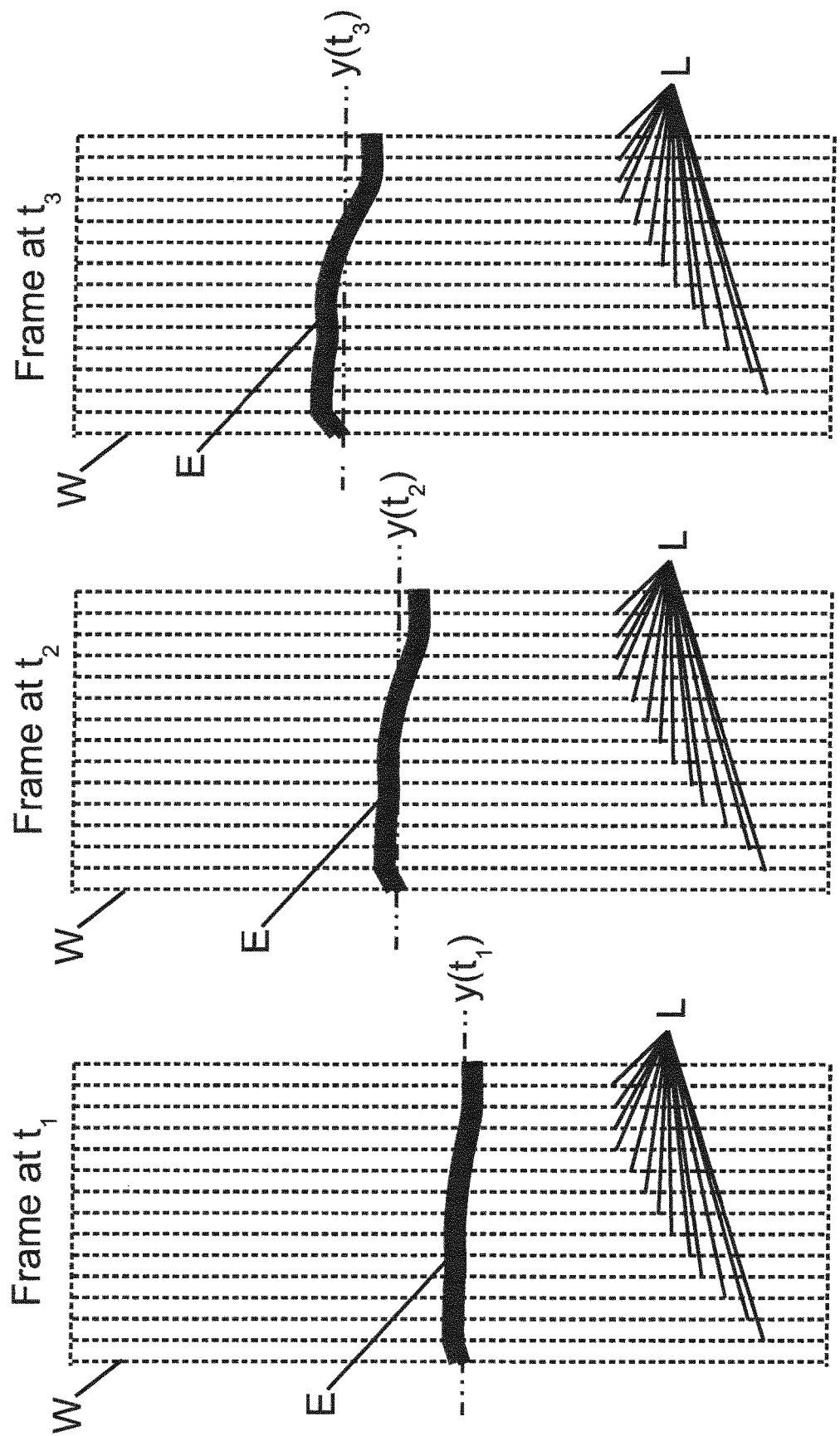
FIG. 3 diagrammatically shows processing of three successive video frames acquired by the camera-based respiratory monitoring device of FIGS. 1 and 2 to extract a respiration-related signal y(t).

With reference now to FIGS. 2 and 3, an illustrative example of evaluating y(t) is described. FIG. 2 diagrammatically shows a perspective view of a suitable placement of the light source 30 of the respiratory monitoring device of FIG. 1. As shown, the beam B produced by the light source 30 is partially occluded by an imaging subject, e.g. by patient P. Specifically, a lower portion of the beam B is blocked by the chest of the patient P while an upper portion of the beam B is not occluded and hence illuminates an opposite portion of the bore wall 20 the line between the shadow and the illumination is the shadow edge E. In a suitable approach, this shadow edge E is analyzed in an analysis window W within the image frame. Said another way, the analysis window W is entirely within the field of view (FOV) of the video camera 40 (see FIG. 1). With reference to FIG. 3, three successive video frames are shown, having respective time stamps $t_1$, $t_2$, and $t_3$. As indicated in FIG. 3, the shadow edge E is not necessarily a perfectly straight line rather, it may have some curvature, and that curvature may vary from one video frame to the next as the chest expands or (partially) deflates. In one suitable edge detection approach, the electronic processor 42 is programmed to extract the position of the edge E of the projected shadow S in each frame of the video by averaging the position of the edge E along each of a plurality of parallel lines L that each intersect the edge E. Said another way, the approach entails determining the one-dimensional position of the edge E of the projected shadow S along each of a plurality of parallel lines L that each intersect the edge E; and averaging the one-dimensional positions of the edge of the projected shadow along the plurality of parallel lines.

Such averaging is computationally fast and provides robustness against possible error sources. In some embodiments, if the sharpness of the shadow (e.g. as defined by the full-width-at-half-maximum of the maximum gradient peak in the gradient image) is below some minimum threshold for one of the lines L then that datum is discarded and the average is taken over the remaining lines L. This is merely an illustrative example, and other approaches can be used for determining y(t) for a given frame t for example, as another approach the entire edge E can be identified and then fitted to a best-fit linear, quadratic, or higher-order polynomial, or to a spline fit or so forth.

Figure 4:
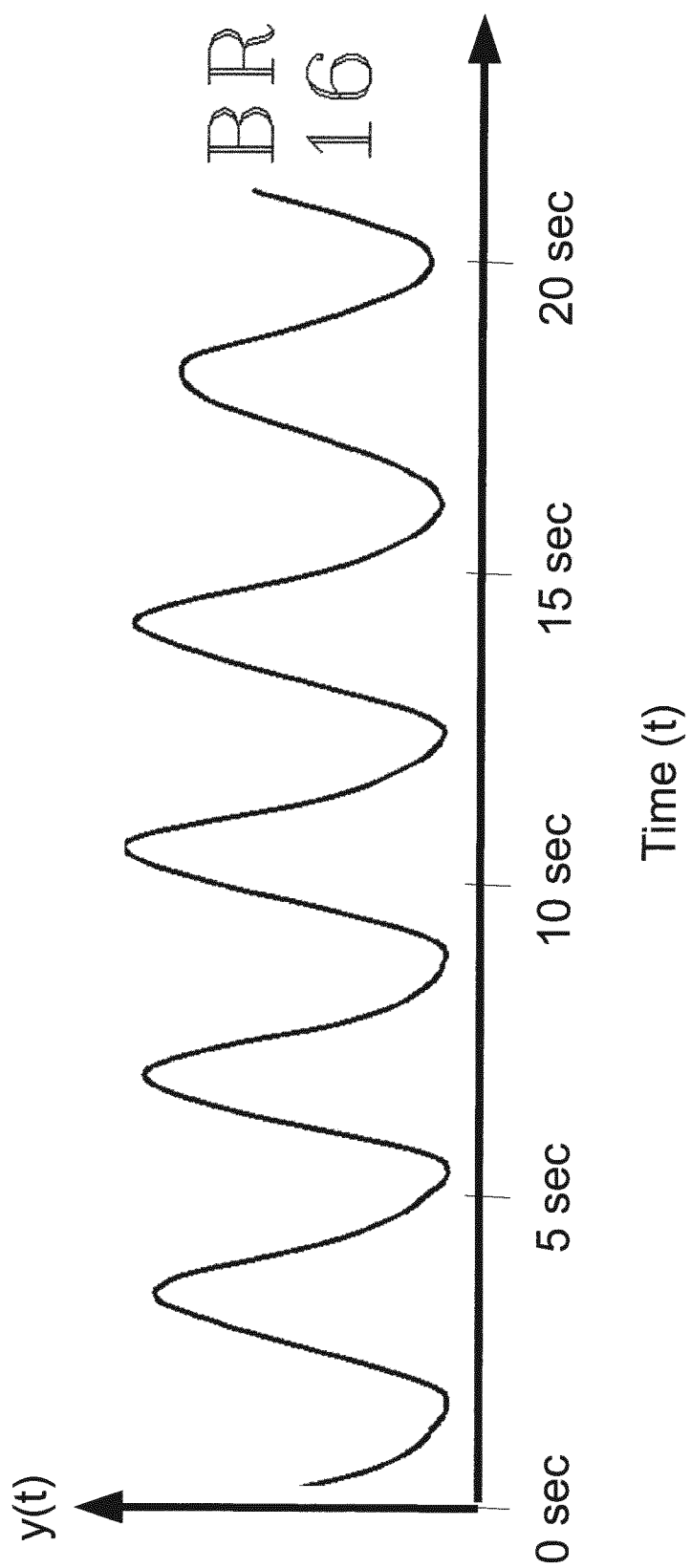
FIG. 4 plots an actually-acquired respiration-related signal y(t) from which the respiratory cycle and the respiration rate (i.e. breathing rate, BR) can be extracted.

With reference to FIG. 4, an actually-acquired breathing data are shown. The breathing signal y(t) was determined from analyzing only the movement of the edge of the shadow of the chest on the wall of the magnet bore of a commercial MR imaging device. In this example, the respiratory rate (i.e. breathing rate) was determined to be 16 breaths per minute.

One factor that may impact effectiveness of the disclosed respiratory monitoring is the choice of the light source 30, and more particularly of the light emission source 34. For example, if the light source 30 emits light similar to that of bore lighting provided to illuminate the patient for the convenience of the imaging technician, then this bore lighting may create additional shadows/lighting that interferes with the respiratory monitoring. One approach is to position the bore lighting at the desired angle to produce the beam B that is, the bore lighting is used as the light source for the respiratory monitoring. In another approach, the light source 30 is chosen to operate at a wavelength or wavelength band that is different from that of the bore lighting (or more generally different from other, potentially interfering, light sources in the imaging facility). For example, the light source 30 may be an infrared light source and likewise the video camera 40 an infrared video camera. If the video camera 40 has spectral filtering to avoid detecting visible light, then this arrangement prevents ambient visible light from interfering with the respiratory monitoring.

The illustrative embodiments employ an imaging device with a bore 10 defining a bore wall 20 used as the "projection screen" for the projected shadow. However, the approach is also usable with imaging modalities that do not provide a defined bore, so long as some surface is available that can serve as the "projection screen". For example, in a digital x-ray system a fixed flat wall may be used as the "projection screen".

The width of the beam B is suitably chosen to provide a relatively sharp shadow edge E, but is preferably also chosen to be a wide beam sufficient to encompass imaging subjects of widely ranging girths. It should be noted that while a sharp shadow edge E is advantageous, some diffuseness of the edge E is permissible so long as the edge E is sufficiently sharp to detect the "up/down" modulation of the subject during respiration.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A respiratory monitoring device configured to operate in conjunction with an imaging device, the respiratory monitoring device comprising:
a light source arranged to generate a projected shadow (S) of an imaging subject (P) positioned for imaging by the imaging device which is projected onto a bore wall of the imaging device;
a video camera arranged to acquire video of the projected shadow on the bore wall; and
an electronic processor programmed to extract a position of an edge of the projected shadow as a function of time from the acquired video by averaging the position of the edge of the projected shadow along each of a plurality of parallel lines that each intersect the edge of the projected shadow.

2. The respiratory monitoring device of claim 1 wherein the electronic processor is programmed to extract the position of the edge (E) of the projected shadow (S) as a one dimensional function of time based on the position of the edge in each frame of the acquired video and time stamps of the video frames.

3. The respiratory monitoring device of claim 1 wherein the light source comprises a projection optic forming the light into a directional beam (B).

4. The respiratory monitoring device of claim 1 wherein the light source comprises an infrared light source and the video camera comprises an infrared video camera.

5. The respiratory monitoring device of claim 1 wherein the electronic processor is further programmed to extract a respiration rate from the extracted position of the edge (E) of the projected shadow (S) as a function of time.

6. The respiratory monitoring device of claim 1 wherein the electronic processor is further operatively connected to control imaging data acquisition intervals over which the imaging device acquires data based on breath-hold or respiratory phase information determined from the extracted position of the edge (E) of the projected shadow (S) as a function of time.

7. A respiratory monitoring device comprising:
an imaging device having a bore wall;
a light source arranged to project a shadow (S) of an associated imaging subject (P) positioned for imaging by the imaging device onto the bore wall of the imaging device, wherein the light source comprises a projection optic forming the light into a directional beam;
a video camera arranged to acquire video of the shadow of the imaging subject projected on the bore wall; and
an electronic processor programmed to extract a position of an edge (E) of the shadow projected onto the bore wall as a function of time from the acquired video.

8. The respiratory monitoring device of claim 7 wherein the electronic processor is programmed to extract the position of the edge (E) of the shadow (S) projected onto the bore wall in each frame of the video by averaging the position of the edge of the shadow projected onto the bore wall along each of a plurality of parallel lines (L) that each intersect the edge of the projected shadow projected onto the bore wall.

9. The respiratory monitoring device of claim 7 wherein the light source comprises an infrared light source and the video camera comprises an infrared video camera.

10. The respiratory monitoring device of claim 7 wherein the electronic processor is further operatively connected with the imaging device to control imaging data acquisition intervals over which the imaging device acquires data based on breath-hold or respiratory phase information determined from the extracted position of the edge (E) of the shadow (S) projected onto the bore wall as a function of time.

11. The respiratory monitoring device of claim 7 wherein the imaging device is one of a magnetic resonance (MR) imaging device, a computed tomography (CT) imaging device, and a positron emission tomography (PET) imaging device.

12. A respiratory monitoring method comprising:
projecting a shadow (S) of an imaging subject (P) positioned for imaging by an imaging device onto a bore wall of the imaging device;
acquiring video of the projected shadow;
extracting a position of an edge (E) of the projected shadow as a function of time from the acquired video by determining a one-dimensional position of the edge (E) of the projected shadow (S) in each frame of the acquired video by determining the one dimensional position of the edge of the projected shadow along each of a plurality of parallel lines (L) that each intersect the edge of the projected shadow and averaging the one dimensional positions of the edge of the projected shadow along the plurality of parallel lines; and
extracting respiratory information from the extracted position of the edge of the projected shadow as a function of time.

13. The respiratory monitoring method of claim 12 wherein the extracting of the position comprises:
determining the position of the edge of the projected shadow as a function of time from the determined one-dimensional positions of the edge in the frames of the acquired video and from time stamps of the video frames.

* * * * *